(12) United States Patent
Vandenburg et al.

(10) Patent No.: US 12,302,492 B2
(45) Date of Patent: May 13, 2025

(54) INTERPOSER FOR ACTIVE IMPLANTABLE MEDICAL DEVICE

(71) Applicant: NeuroPace, Inc., Mountain View, CA (US)

(72) Inventors: Joseph Vandenburg, Bethesda, MD (US); Dennis Potts, Scotts Valley, CA (US)

(73) Assignee: NeuroPace, Inc., Mountain View, CA (US)

( * ) Notice: Subject to any disclaimer, the term of this patent is extended or adjusted under 35 U.S.C. 154(b) by 569 days.

(21) Appl. No.: 17/547,043

(22) Filed: Dec. 9, 2021

(65) Prior Publication Data

US 2022/0192019 A1    Jun. 16, 2022

Related U.S. Application Data

(60) Provisional application No. 63/126,407, filed on Dec. 16, 2020.

(51) Int. Cl.
*H05K 1/11*    (2006.01)
*A61N 1/375*    (2006.01)

(52) U.S. Cl.
CPC ............ *H05K 1/111* (2013.01); *A61N 1/3754* (2013.01); *H05K 1/117* (2013.01); *H05K 2201/10378* (2013.01)

(58) Field of Classification Search
CPC ..................... H05K 1/111; H05K 1/117; H05K 2201/10378; A61N 1/3754
See application file for complete search history.

(56) References Cited

U.S. PATENT DOCUMENTS

| 7,623,335 | B2 | 11/2009 | Stevenson et al. |
| 8,644,936 | B2 | 2/2014 | Iyer et al. |
| 9,627,833 | B2 | 4/2017 | Miltich et al. |
| 2005/0007718 | A1* | 1/2005 | Stevenson ............ A61N 1/3754 361/118 |
| 2013/0060312 | A1* | 3/2013 | Iyer ........................ H05K 13/00 607/116 |

(Continued)

FOREIGN PATENT DOCUMENTS

| EP | 3069753 A1 | 9/2016 |
| WO | 2016113638 A1 | 7/2016 |

*Primary Examiner* — Michael P McFadden
(74) *Attorney, Agent, or Firm* — LOZA & LOZA, LLP; David S. Sarisky

(57) ABSTRACT

A printed circuit assembly (PCA) for coupling to an IMD feedthrough of an implantable medical device includes a PCB portion and an interposer. The IMD feedthrough has a support structure and a plurality of electrical contacts extending through the support structure. The PCB portion is configured to be arranged relative to the support structure of the IMD feedthrough and includes a plurality of electrical contacts. The interposer is secured to the PCB portion and includes a dielectric over-mold structure and a plurality of leads. Each lead is integrated with the dielectric over-mold structure and includes a weld pad and a solder pad. Each solder pads of the interposer is electrically coupled to a corresponding electrical contacts of the PCB portion to provide an alignment between one or more weld pads of the interposer and one or more corresponding electrical contacts of the IMD feedthrough.

14 Claims, 12 Drawing Sheets

(56) References Cited

U.S. PATENT DOCUMENTS

| | | | |
|---|---|---|---|
| 2013/0138186 A1* | 5/2013 | Iyer | A61N 1/05 |
| | | | 607/116 |
| 2013/0138187 A1* | 5/2013 | Iyer | A61N 1/3754 |
| | | | 607/116 |
| 2013/0176658 A1* | 7/2013 | Iyer | H01G 2/04 |
| | | | 361/302 |
| 2013/0231718 A1* | 9/2013 | Imani | H01R 13/7195 |
| | | | 29/857 |
| 2015/0245468 A1* | 8/2015 | Barry | H05K 3/32 |
| | | | 174/257 |
| 2016/0287883 A1* | 10/2016 | Barry | H05K 5/0247 |
| 2017/0080239 A1 | 3/2017 | Seitz et al. | |
| 2018/0304084 A1 | 10/2018 | Stevenson et al. | |

\* cited by examiner

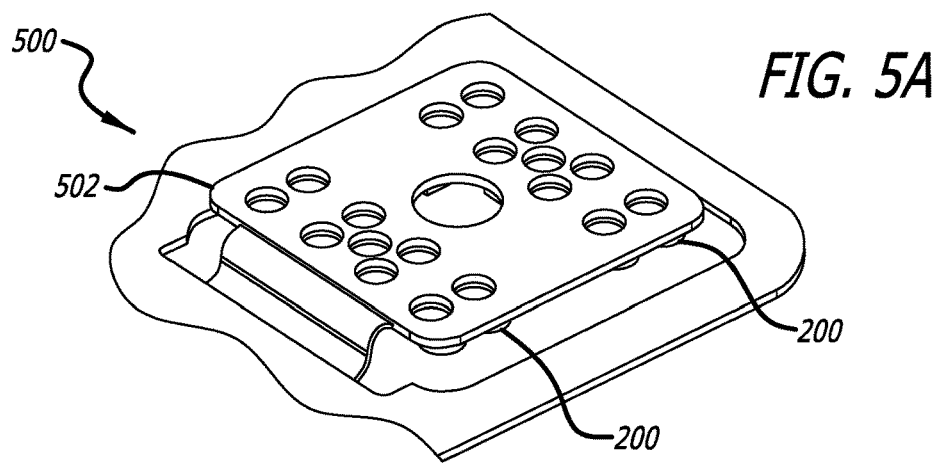
*FIG. 5A*
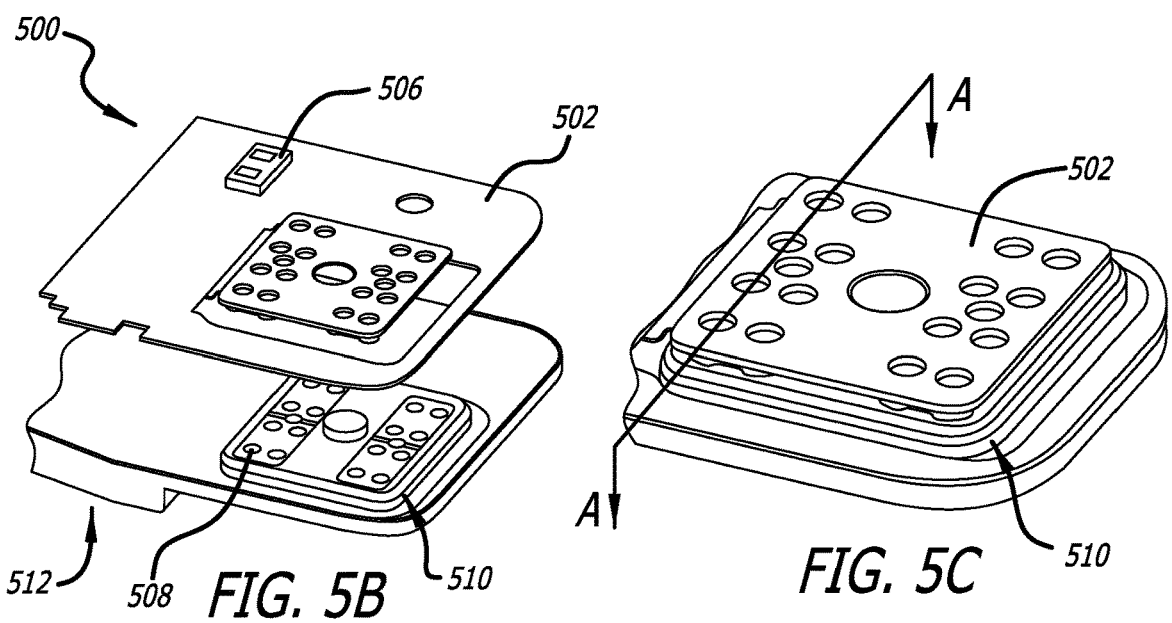
*FIG. 5B*   *FIG. 5C*
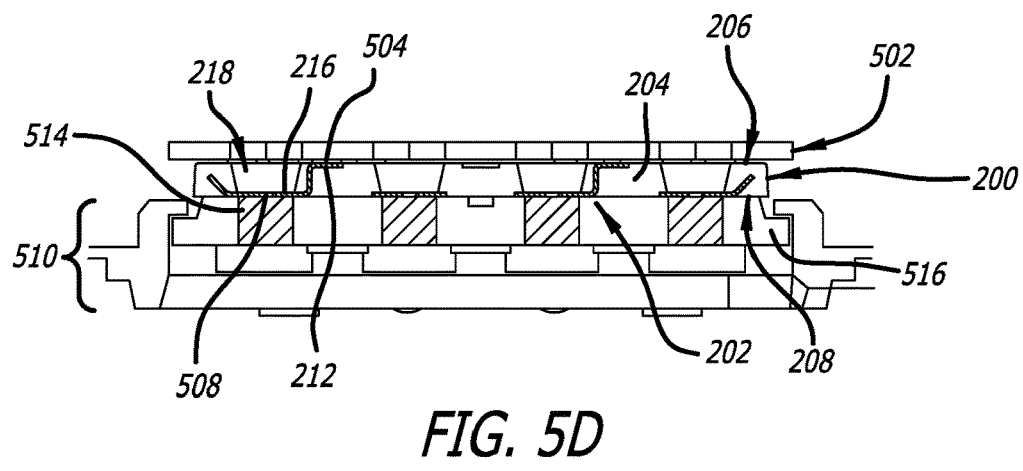
*FIG. 5D*

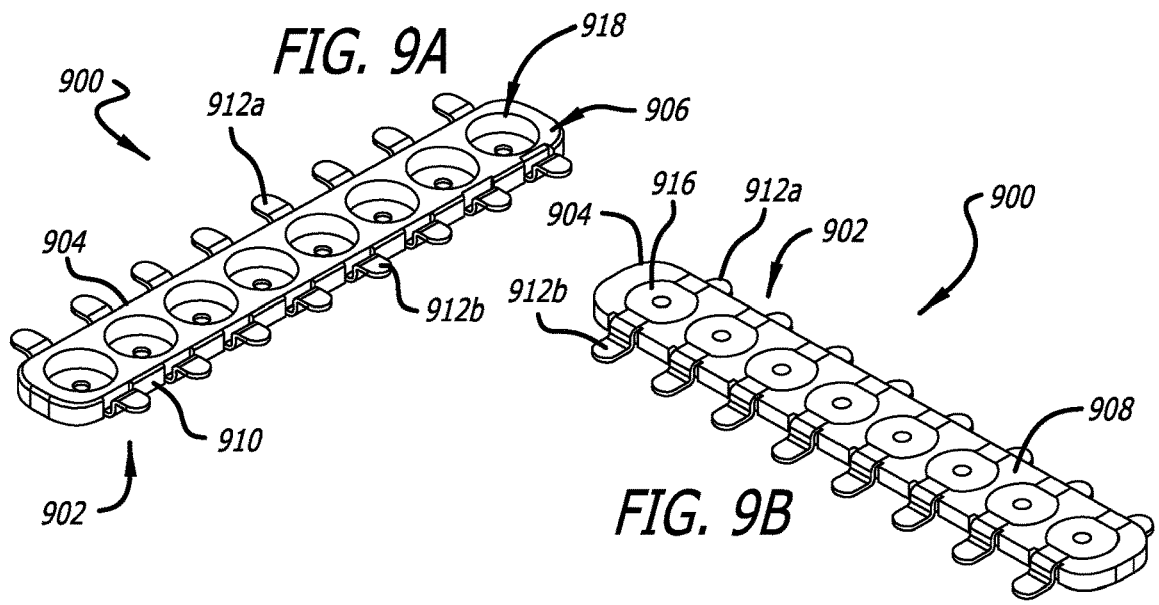
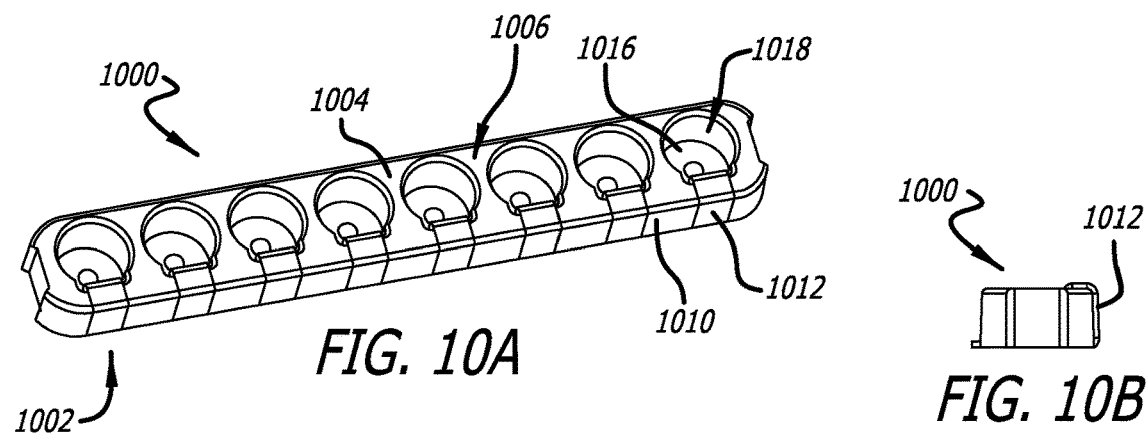
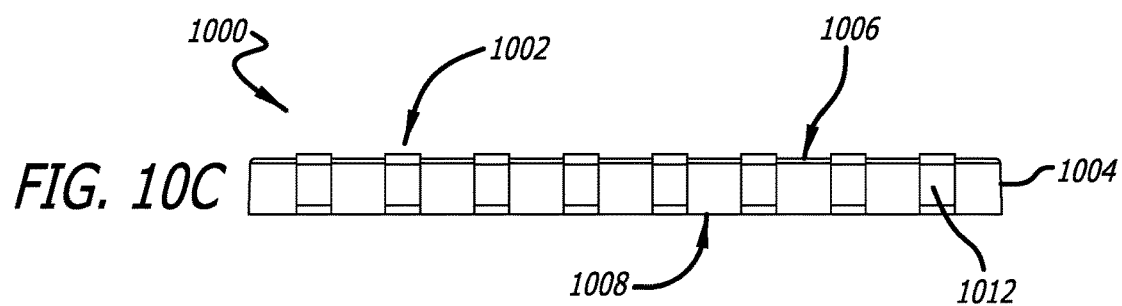
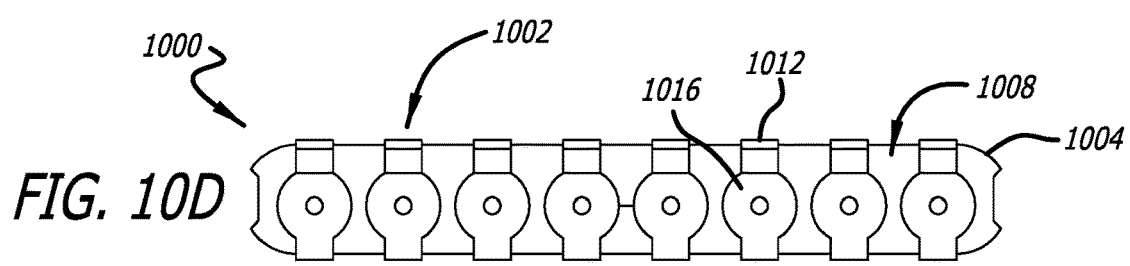

INTERPOSER FOR ACTIVE IMPLANTABLE MEDICAL DEVICE

CROSS-REFERENCE TO RELATED APPLICATION(S)

This application claims the benefit of and priority to U.S. Provisional Patent Application Ser. No. 63/126,407, filed Dec. 16, 2020, for "Interposer for Active Implantable Medical Device and Method of Manufacture", the entire disclosure of which is incorporated herein by reference.

TECHNICAL FIELD

The present disclosure relates generally to active implantable medical devices, and more particularly, to an electrical interposer between an hermetic feedthrough and a printed circuit assembly of an active implantable device.

BACKGROUND

Known techniques for providing electrical interconnections between a feedthrough and a printed circuit assembly (PCA) of an implantable medical device are diverse and may be categorized as follows:

With reference to FIG. 1A, electrical interconnections between a feedthrough of an active implantable medical device and a PCA is provided by a flex band. Note, in FIG. 1A, the flex band between the feedthrough and the PCA is bound by dashed lines and is illustrated transparent to reveal underlying components. The flex band consists of nickel traces secured by acrylic adhesive between layers of polyamide, e.g. Kapton. As oriented in FIG. 1A, a portion of the flex band is located on top of a feedthrough and is electrically coupled to feedthrough pins that extend through holes in the flex band. Traces within the flex band extend from the feedthrough pins to flex wires that couple to another portion of the flex band that, in turn, electrically couples with circuitry of the PCA. Electrical interconnection between the circuitry of the PCA and the flex band may be made by laser welds between the flex band and weld tabs of the PCA.

With reference to FIG. 1B, wire bonding is a common technique in making an electrical connection between a feedthrough and a PCA in an active implantable device. Wire bonding involves the attachment of two adjacent pads (e.g., solder pads and feedthrough pins) with a small (0.0015-0.30 mm) wire of gold, copper, aluminum or silver. The feedthrough and PCA are designed with the pads on parallel planes to facilitate the wire bonding process. A feedthrough with filter capacitors mounted directly onto the feedthrough provide a means of connecting the feedthrough conductors to a PCA. Termination through a filter capacitor supports both direct solder connections and the wire bonding process. With reference to FIG. 1B, interconnect wires may be soldered to solder pads on a PCA and resistance welded to feedthrough pins.

With reference to FIG. 1C, a ball grid array (BGA) surface mount package comprising a dielectric substrate and electrically conductive solder balls on one side and electrically conductive pads on the opposite side provides a means of making an electrical connection between two parallel components, e.g., a die and a printed circuit board (PCB). The electrical connection between the die and PCB is completed through bonding wires and the die and pads are encapsulated in epoxy.

With reference to FIG. 1D, an interconnect structure having elastically compliant electrical conductors, such as pogo pins or leaf springs, fixed to a dielectric substrate provides a means of making an electrical connection between opposing substrates, e.g., a target substrate and a PCB. Three different configurations of spring loaded interconnect structures are shown in FIG. 1D. In one configuration (far left), the elastically compliant electrical conductors are spring loaded at the end facing the target and are electrically coupled, e.g. soldered, at the non-spring loaded end to pads on the PCB prior to coupling with pads on the target. In the other two configurations (center and far right), the elastically compliant electrical conductors are spring loaded at both ends and no soldering occurs. Each of these spring loaded interconnect structures require mechanical clamping between the opposed target substrate and the PCB to maintain electrical conductivity.

SUMMARY

One aspect of the disclosure relates to a printed circuit assembly (PCA) for coupling to an IMD feedthrough of an implantable medical device. The IMD feedthrough has a support structure and a plurality of IMD electrical contacts extending through the support structure. The PCA includes a PCB portion and an interposer. The PCB portion is configured to be arranged relative to the support structure of the IMD feedthrough and includes a plurality of PCB electrical contacts. The interposer is secured to the PCB portion and includes a dielectric over-mold structure and a plurality of leads. The number of leads may correspond in number to the plurality of PCB electrical contacts. Each lead is integrated with the dielectric over-mold structure and includes a weld pad and a solder pad. Each solder pad of the interposer is electrically coupled to a corresponding PCB electrical contact to provide an alignment between one or more weld pads of the interposer and one or more corresponding IMD electrical contacts of the IMD feedthrough. The alignment may be any one of several configurations including, for example, an axial alignment, orthogonal alignment, or an angular alignment between axial and orthogonal.

One aspect of the disclosure relates to an interposer including a dielectric over-mold structure and a plurality of conductive leads integrated with the dielectric over-mold structure. The dielectric over-mold structure includes a weld-pad surface, a solder-pad surface opposite the weld-pad surface, a perimeter surface around the perimeter of the dielectric over-mold structure that is generally orthogonal to the weld-pad surface and the solder-pad surface, and a plurality of weld-pad vias associated with the solder-pad surface. Each of the conductive leads integrated with the dielectric over-mold structure includes a solder pad, a weld pad having at least one surface exposed through one of the plurality of weld-pad vias, and a portion connecting the weld pad with the solder pad.

One aspect of the disclosure relates to an implantable medical device comprising a feedthrough, a printed circuit assembly (PCA), and in interposer. The feedthrough includes a support structure and a plurality of electrical contacts extending through the support structure. The PCA includes a feedthrough portion arranged generally parallel relative to the support structure. The feedthrough portion of the PCA has a plurality of PCA electrical contacts. The interposer is arranged generally parallel relative to the support structure of the feedthrough and the feedthrough portion of the PCA. The interposer includes a plurality of leads corresponding in number to the plurality of electrical contacts of the feedthrough. Each lead is fixedly secured relative to an over-mold structure, and has a weld pad electrically coupled to an electrical contact of the feedthrough, and a solder pad electrically coupled to a PCA electrical contact of the PCA.

One aspect of the disclosure relates to an implantable medical device comprising a printed circuit assembly (PCA) with a printed circuit board (PCB), and one or more single pin connectors associated with the PCB. Each of the one or more single pin connectors is electrically coupled to a component of the implantable medical device. The medical device also includes one or more single pin interposers comprising a weld pad electrically coupled to one of the one or more single pin connectors, and at least one leg electrically coupled between the weld pad and the PCB. The at least one leg is arranged to offset the weld pad from the PCB.

It is understood that other aspects of apparatuses will become readily apparent to those skilled in the art from the following detailed description, wherein various aspects of apparatuses are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of apparatuses will now be presented in the detailed description by way of example, and not by way of limitation, with reference to the accompanying drawings, wherein:

FIG. 5A is an illustration of a PCA including a pair of interposers on the underneath side of the PCA and electrically coupled to a PCB portion of the PCA.

FIGS. 5B and 5C are illustrations of the PCA of FIG. 5A integrated into an implantable medical device having a leadless feedthrough.

FIG. 5D is a cross-section illustration of the PCA and feedthrough of FIG. 5C along line A-A.

FIGS. 9A and 9B are illustrations of an interposer of the present disclosure having leads with portions that are externally routed over the over-mold structure to define a pair of opposed solder pads for each lead.

FIGS. 10A-10D are illustrations of an interposer of the present disclosure having a single linear array of leads, each lead with a portion that is externally routed over the over-mold structure to achieve a single solder pad for each lead.

DETAILED DESCRIPTION

Figure 1A:
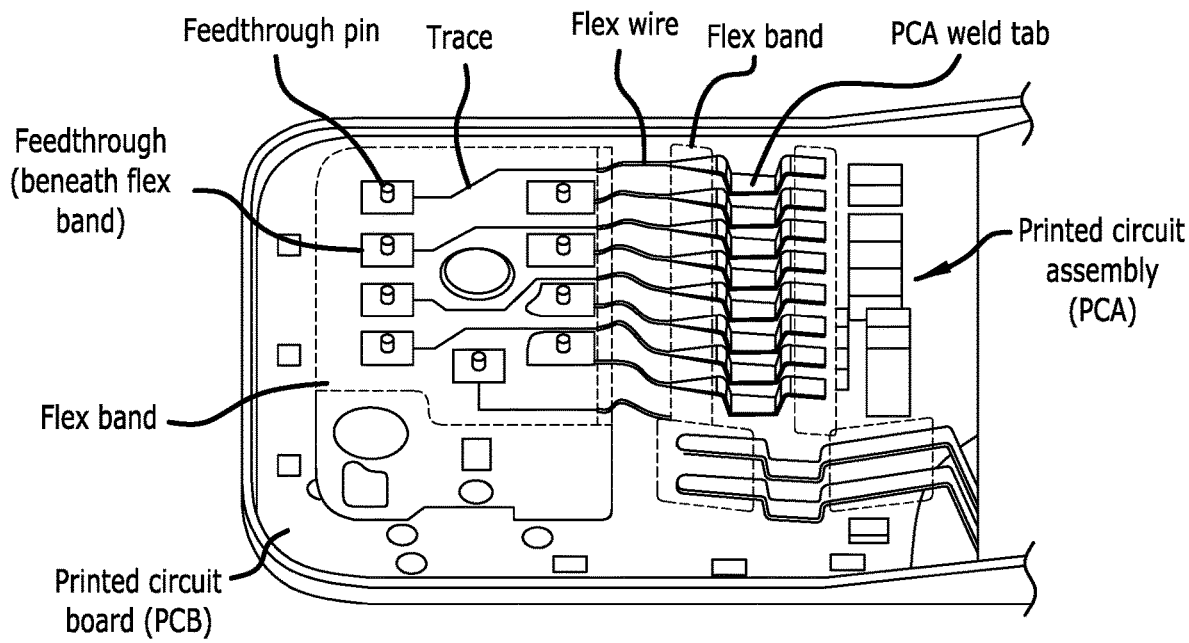
FIG. 1A is an illustration of an active implantable medical device wherein electrical interconnections between a feedthrough and a printed circuit assembly (PCA) are provided by a flex band that extends between the feedthrough and the PCA.
Figure 1B:
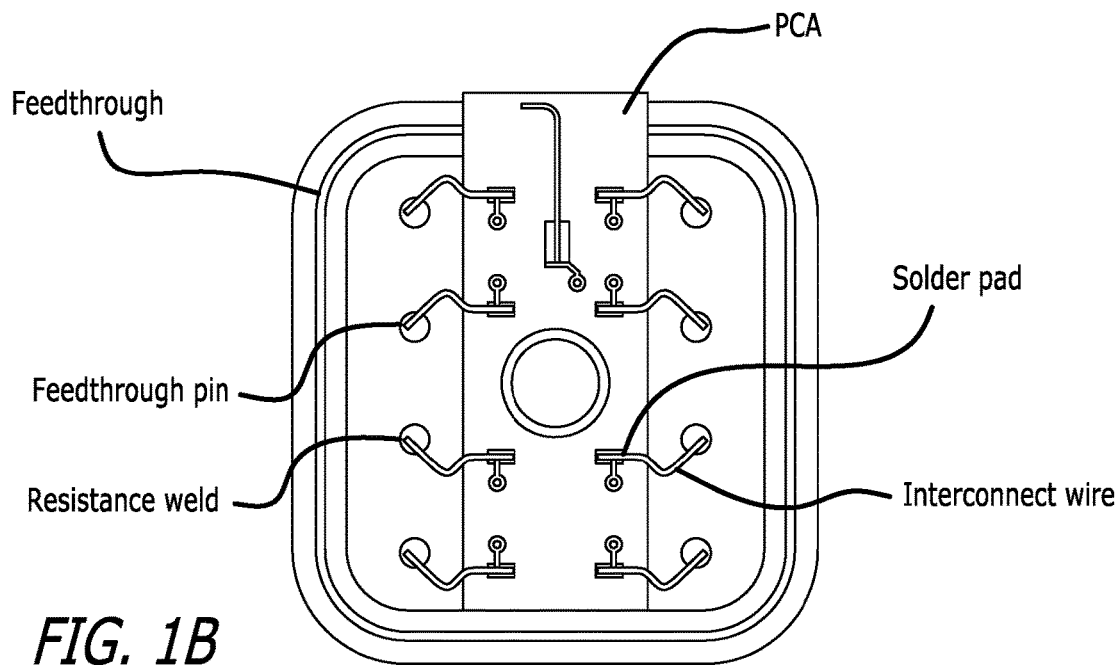
FIG. 1B is an illustration wherein electrical interconnections between a feedthrough and a PCA are provided by interconnect wires that are soldered to solder pads on the PCA and resistance welded to feedthrough pins of the feedthrough.
Figure 1C:
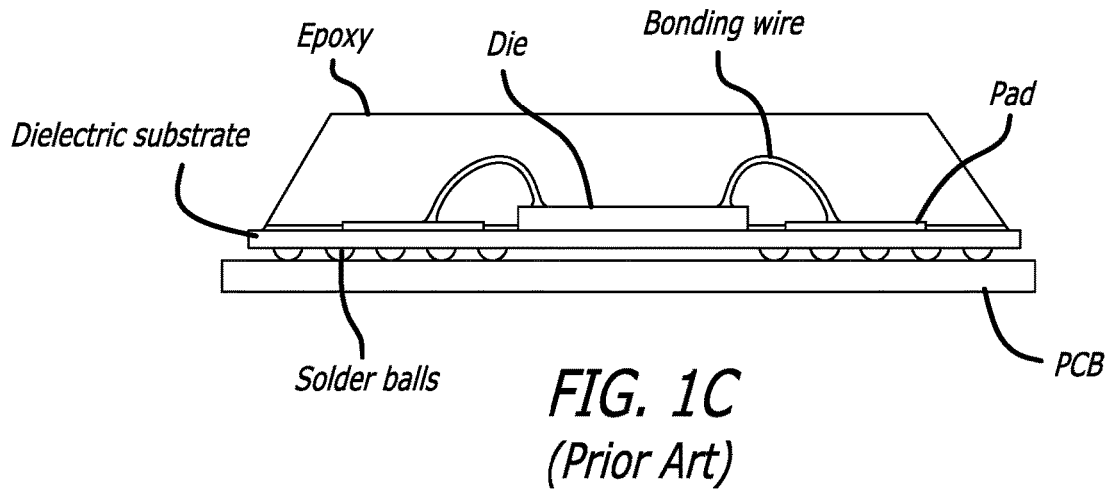
FIG. 1C is an illustration of ball grid array (BGA) surface mount package wherein electrical interconnections between a die and a printed circuit board (PCB) are provided by a dielectric substrate and electrically conductive solder balls and pads on opposite sides of the substrate.
Figure 1D:
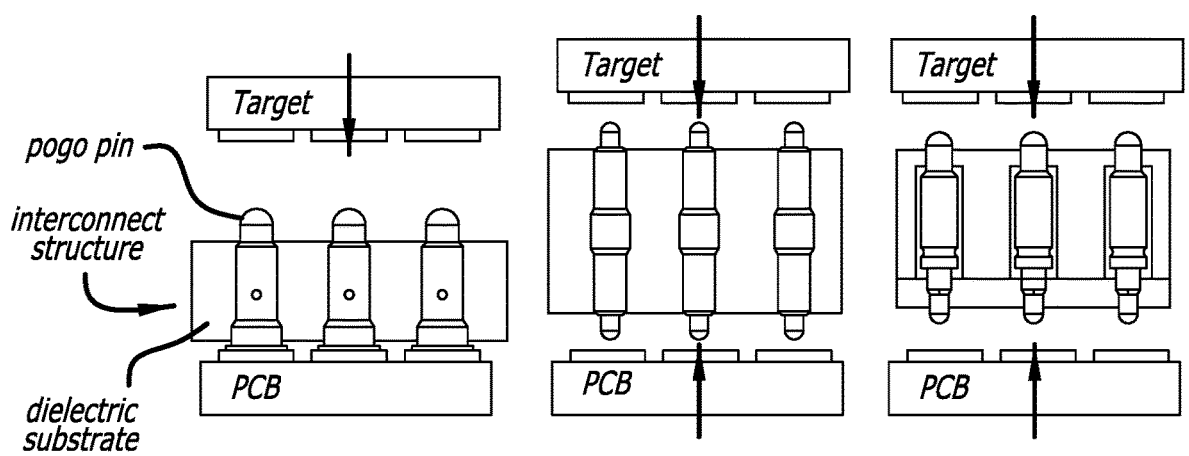
FIG. 1D are illustrations of different interconnect structures wherein electrical interconnections between a target substrate and a printed circuit board (PCB) are provided by elastically compliant conductors associated with a dielectric substrate.
Figure 2A:
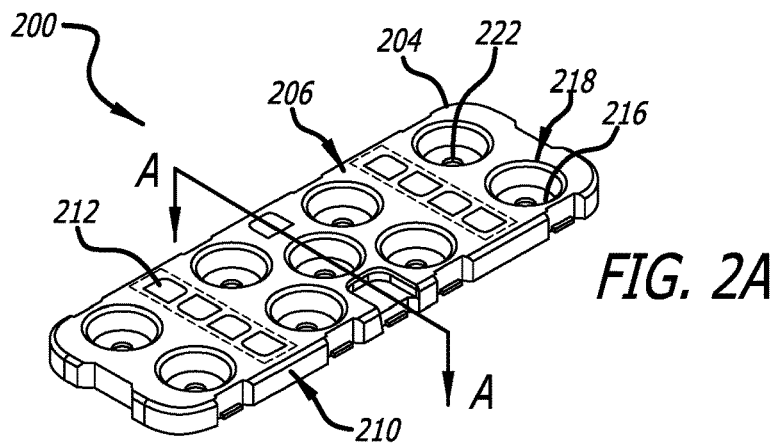
FIGS. 2A-2C are illustrations of an interposer of the present disclosure for an active implantable medical device having a plurality of electrically conductive leads embedded in an over-mold structure.
Figure 2B:
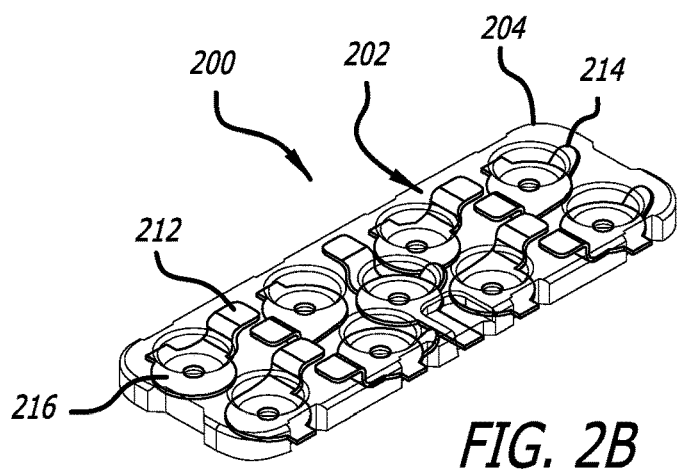
Figure 2C:
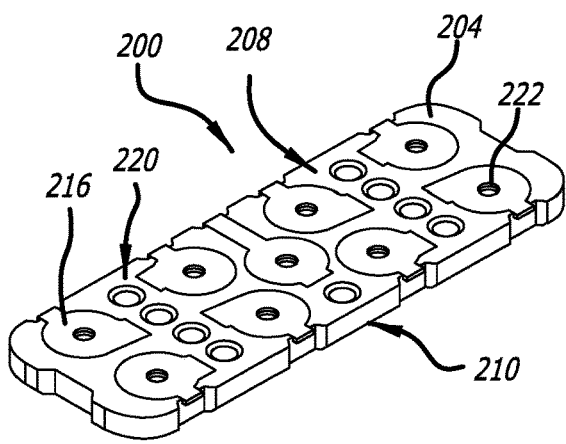
Figure 2D:
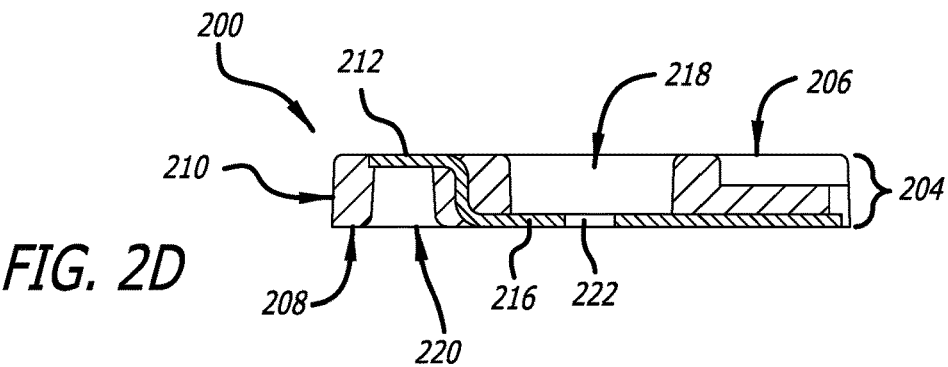
FIG. 2D is a cross-section illustration of the interposer of FIG. 2A along line A-A.

With reference to FIGS. 2A-2D, an interposer 200 for an active implantable medical device includes a plurality of electrically conductive leads 202 at least partially embedded in an over-mold structure 204 of dielectric material. In FIG. 2B, the over-mold structure 204 of the interposer 200 is illustrated transparent to reveal nine leads 202 within the over-mold structure. Normally the over-mold structure 204 is opaque as shown in FIGS. 2A, 2C and 2D.

The leads 202 are formed from a sheet metal of an electrically conductive ductile alloy such as nickel or a nickel-copper alloy and include a solder pad 212, a locking tab 214, and a weld pad 216. The leads 202 may be coated or plated to inhibit oxidation of the base material and improve the adhesion to molten solder. A common coating is electroless-nickel immersion gold (ENIG). As described further below, the solder pads 212 and weld pads 216 of each lead 202 define an electrically conductive pad of the interposer 200.

The over-mold structure 204 comprises a thermoplastic such as polyetheretherketone (PEEK) or Liquid Crystal Polymer (LCP), or thermoset such as glass filled epoxy. The over-mold structure 204 may be referred to herein as a dielectric substrate.

During manufacture of the interposer 200, the material forming the over-mold structure 204 is molded over a lead frame that includes the plurality of leads 202 to fix and unify the over-mold material and the lead frame into a unitary, single component. As shown in FIG. 2B, locking tabs 214 may be formed into the lead frame. The locking tabs 214 aide in securing the lead frame into the over-mold structure 204.

Continuing with reference to FIGS. 2A-2D, the interposer 200 includes a solder-pad surface 206, a weld-pad surface 208 opposite the solder-pad surface and a perimeter surface 210 that extends around the perimeter of the interposer. The solder-pad surface 206 includes exposed portions of the leads 202 corresponding to the solder pads 212. The solder pads 212 may be coated with solder or may be prepared to wet to solder, for example, by applying an electroless nickel immersion gold (ENIG) coating. The solder pads 212 of the interposer 200 enable the interposer to be reflow-soldered to a printed circuit assembly. As shown in FIG. 2D, the interposer 200 includes a number of solder-pad vias 220, each having an end that exposes a surface of a corresponding solder pad 212.

Continuing with FIG. 2D, the weld-pad surface 208 of the interposer 200 includes exposed portions of the leads 202 corresponding to the weld pads 216. The weld pads 216 may be placed on either a flat surface to be laser welded or over a feedthrough pin which could be laser welded onto the pad. The weld pads 216 may include a hole 222 for receiving a feedthrough pin. As shown in FIG. 2A, the over-mold structure 204 includes a number of weld-pad vias 218, each having an end that exposes a surface of a corresponding weld pad 216.

Manufacturing of Interposer

Figure 3A:
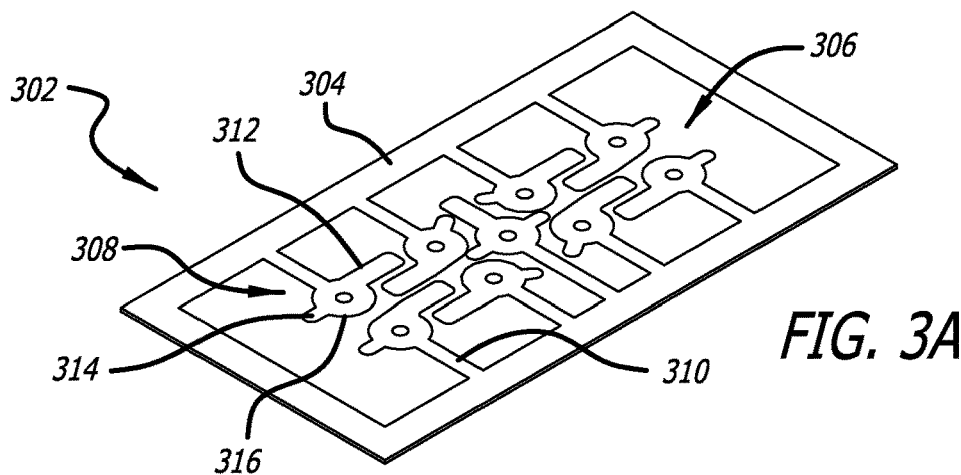
FIGS. 3A and 3B are illustrations of a flat lead frame formed when manufacturing the interposer of FIGS. 2A-2D and having a perimeter surrounding a plurality of flat lead structures.
Figure 3B:
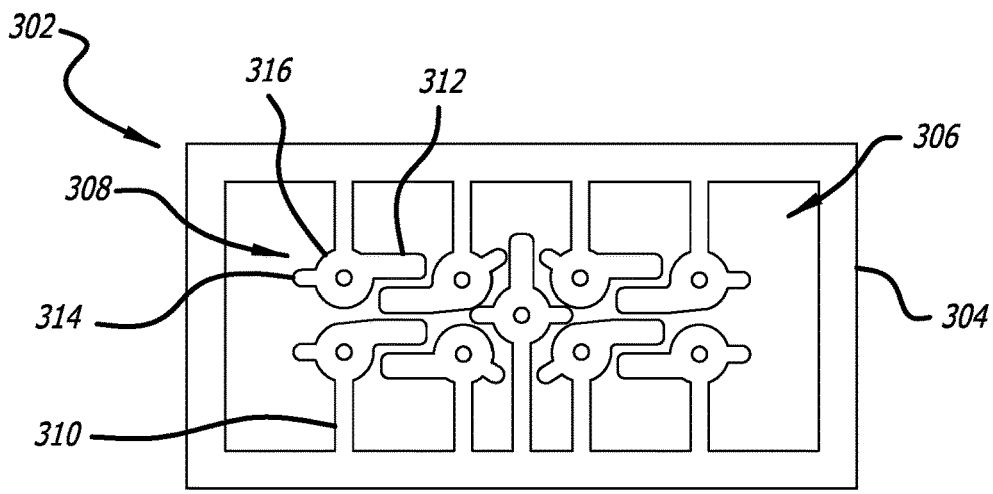

The process for manufacturing an interposer 200 of FIGS. 2A-2D is as follows:

With reference to FIGS. 3A and 3B, a flat sheet of a conductive alloy material is etched, laser cut or die punched to create a flat lead frame 302 having a perimeter 304 and an interior portion 306. In one configuration, the flat lead frame 302 has a thickness in the range of 0.013-0.130 mm. The range of thickness, however, may be greater for a larger configuration of this type of part in larger assemblies. To improve wetting to solder in a finished interposer 200 the flat sheet of alloy material may be prepared with an ENIG coating prior to fabricating the flat lead frame 302.

Figure 3C:
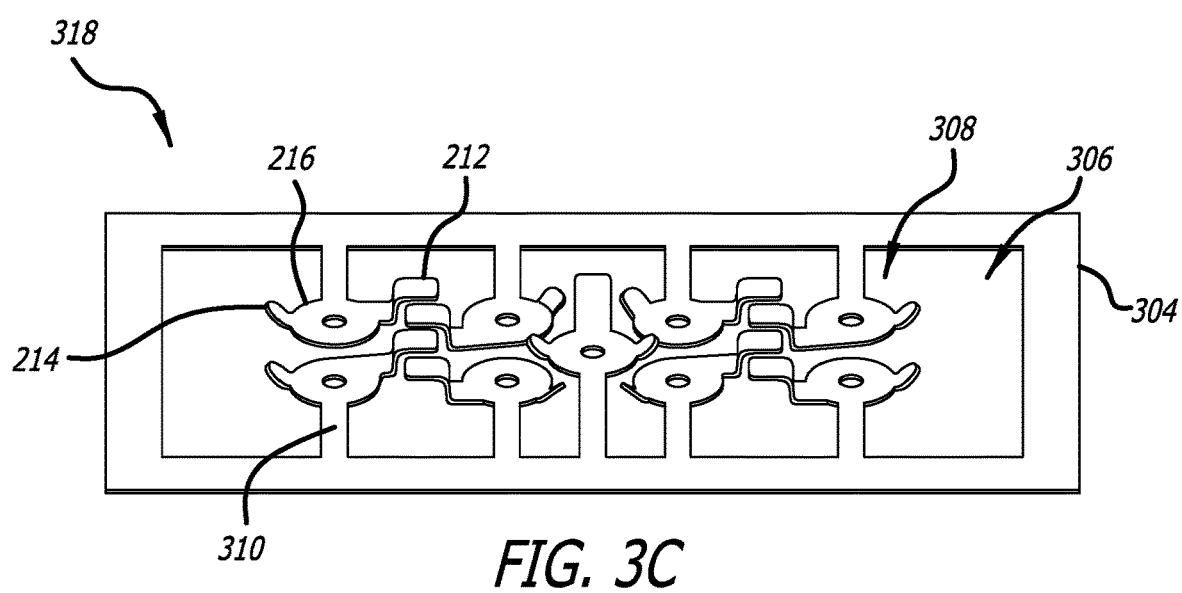
FIG. 3C is an illustrations of a formed lead frame that results from bending portions of the flat lead structures of FIGS. 3A and 3B.

The interior portion 306 of the flat lead frame 302 includes a number of flat lead structures 308, each suspended within the perimeter 304 by a support tab 310. These flat lead structures 308 include portions 312, 314, 316 that form the solder pads 212, the locking tabs 214, and the weld pads 216 of the interposer. With reference to FIGS. 3C, the flat lead frame 302 of FIGS. 3A and 3B is formed into a formed lead frame 318 by bending portions 312, 314 of the flat lead structures 308 with a forming tool. The bent portions 312, 314 of the formed lead frame 318 form part of the solder pads 212 and locking tabs 214 of the interposer 200. Unbent portions 316 of the formed lead frame 318 form the weld pads 216.

Figure 3D:
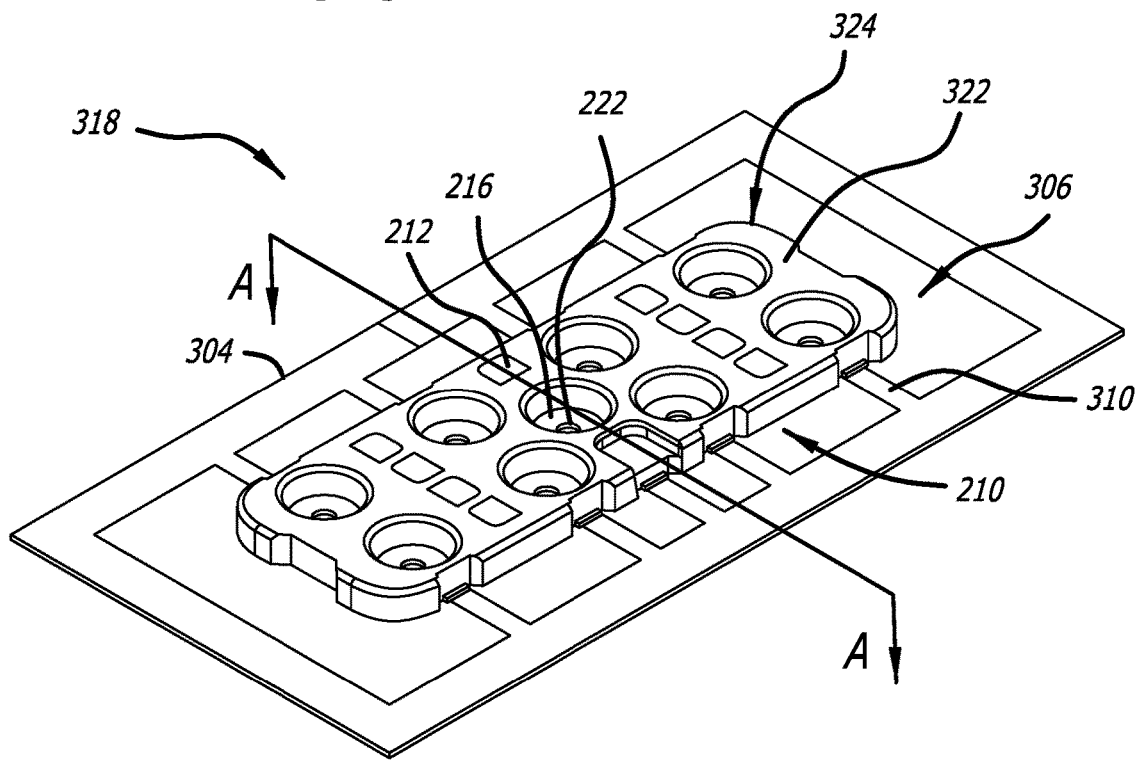
FIG. 3D is an illustration of the formed lead frame of FIG. 3C, wherein the formed lead structures of FIG. 3C are over molded with a dielectric material.
Figure 3E:
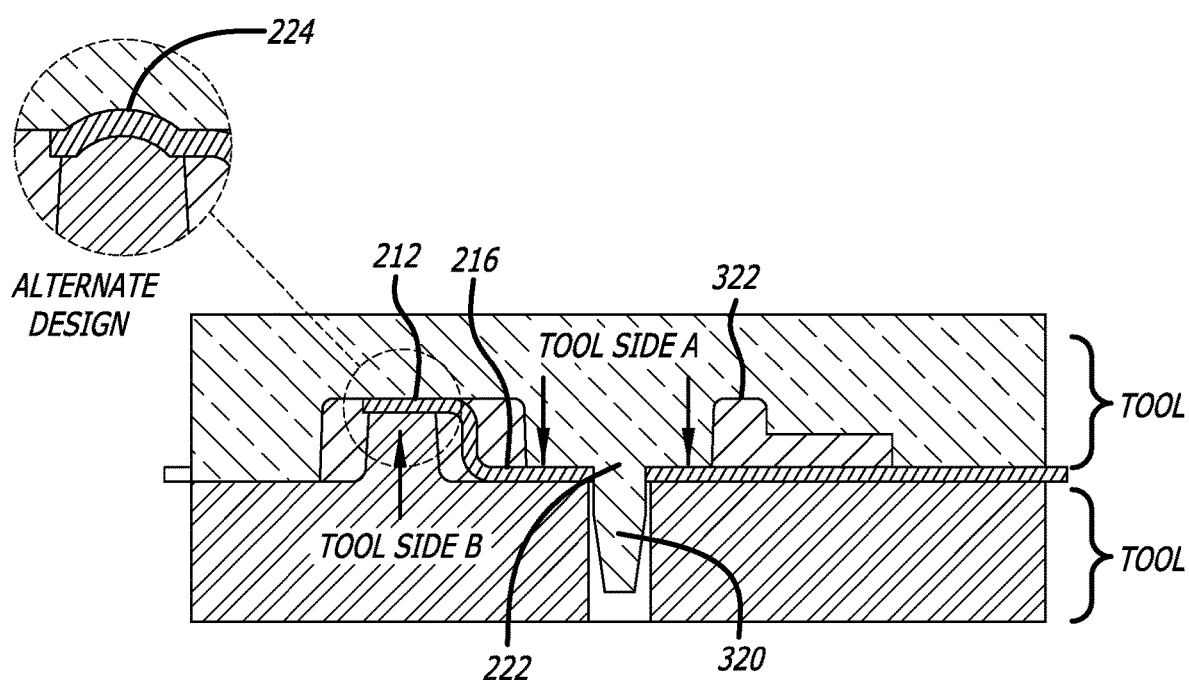
FIG. 3E is a cross-section illustration of the formed lead frame and dielectric over-mold of FIG. 3D along line A-A, with further illustration of an over mold tool used during manufacture.

With reference to FIGS. 3D and 3E, the formed lead frame 318 is over-molded with a dielectric material 322 to form a unitary, single-piece structure 324 at the interior portion 306 of the frame. The dielectric material may be, for example, a molten polymer. The over-mold process involves placing the formed lead frame 318 in an injection molding tool having opposed sides A and B (portions of which are shown in FIG. 3E). The formed lead frame 318 may be positioned on pins 320 of the molding tool which protrude through the holes 222 in the weld pads 216. As the over-mold tool is closed, features in the molding tool press the formed lead frame 318 against the opposite side of the mold, ensuring shut-off of the dielectric material 322 and precision thickness of the unitary, single-piece structure 324. Injection mold equipment is employed to inject molten polymer into the mold around the interior portion 306 of the formed lead frame 318 which cools and locks the interior portion of the lead frame into the molded material.

Figure 3F:
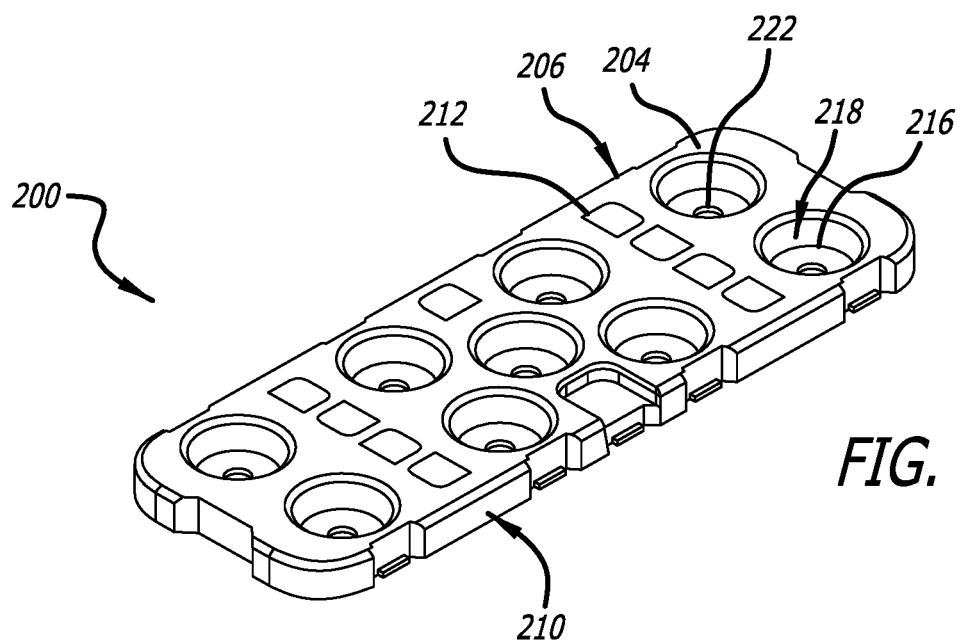
FIG. 3F is an illustration of an interposer (oriented such that its solder-pad surface is visible) that results when the over-molded interior structure of FIG. 3D is separated from the lead frame.
Figure 3G:
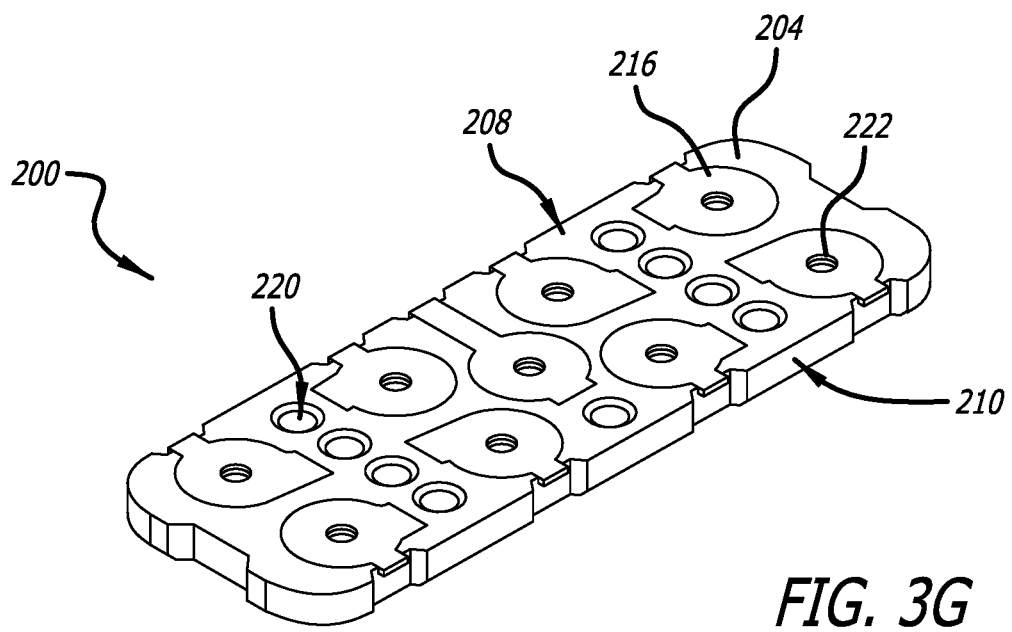
FIG. 3G is an illustration of an interposer (oriented such that its weld-pad surface is visible) that results when the over-molded interior structure of FIG. 3D is separated from the lead frame.

With reference to FIGS. 3D, 3F and 3G, the support tabs 310 of the formed lead frame 318 are trimmed from the unitary, single-piece structure 324 at the end of the tabs adjacent the perimeter surface 210 of the structure to thereby separate the structure from the support tabs and the perimeter 304 of the formed lead frame. Trimming methods include laser cutting or hard stamping trim tooling.

Once separated, the unitary, single-piece structure 324 forms the interposer 200 of FIGS. 2A-2D.

With reference to FIG. 3E, in some embodiments the solder pads 212 may include a dimple 224 defined by a raised section to improve solderability to a printed circuit assembly. The dimple 224 may be formed during the forming of the formed lead frame 318, prior to over-molding, or during the over-mold process. If the dimple 224 is formed during the over-mold process, the features in the mold which press the formed lead frame 318 against the opposite side of the mold may include features which would simultaneously form the dimple 224 into the solder pad 212. Corresponding recesses in the opposite side of the mold may be used to form the dimpled solder pads 212.

Interposer Integration with Active Implantable Medical Device

The interposer 200 disclosed herein is configured for integration with various configurations of active implantable medical devices having feedthrough assemblies that couple to electrically conductive leads. For example, as described below with reference to FIGS. 4A-4C, the interposer 200 may be integrated into an implantable medical device having a feedthrough assembly with pins. In another example described below with reference to FIGS. 5A-5D, the interposer 200 may be integrated into an implantable medical device having a high temperature co-fired feedthrough technology, known as a leadless or pinless feedthrough.

Figure 4A:
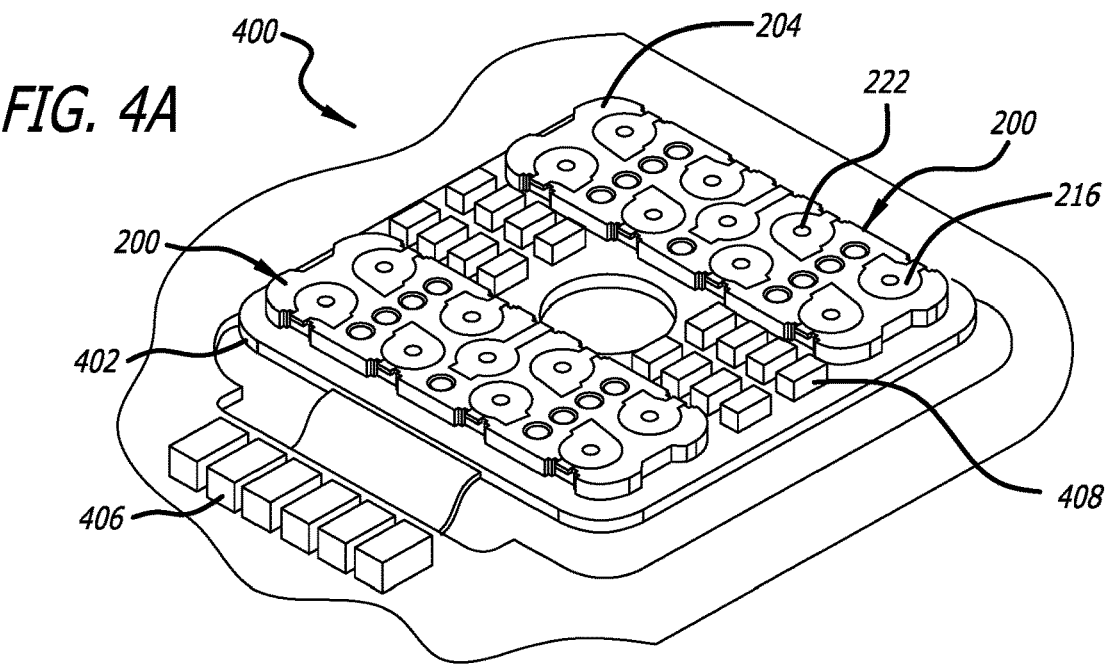
FIG. 4A is an illustration of a PCA including a pair of interposers oriented as shown in FIG. 3G and electrically coupled to a printed circuit board (PCB) portion of the PCA.
Figure 4B:
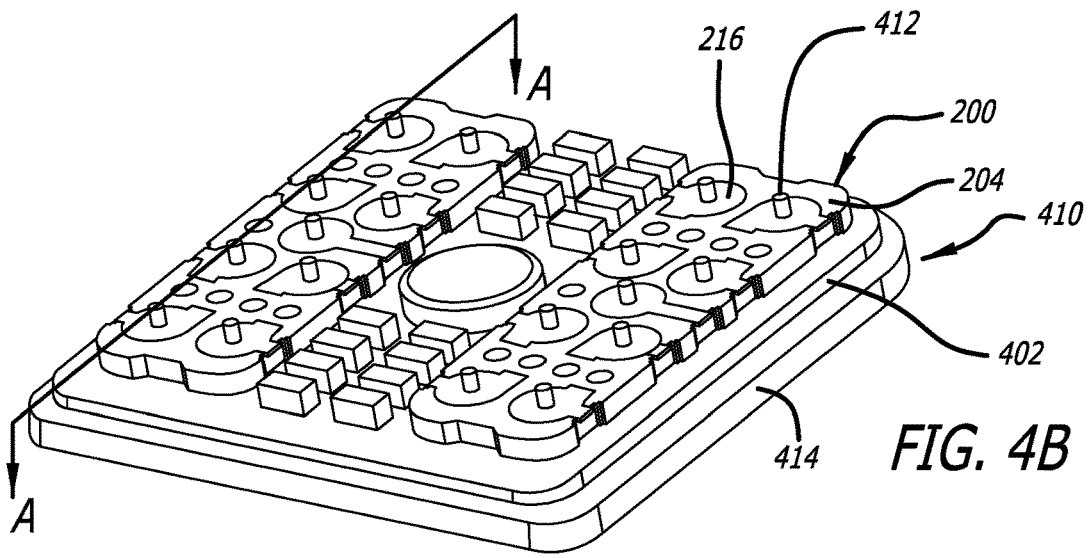
FIG. 4B is an illustration of the PCA of FIG. 4A integrated into an implantable medical device having a feedthrough with pins.
Figure 4C:
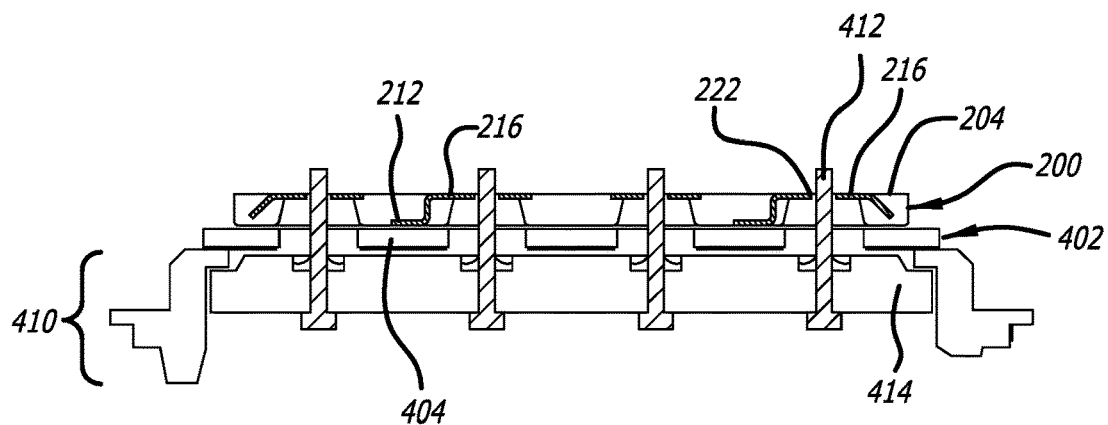
FIG. 4C is a cross-section illustration of the PCA and feedthrough of FIG. 4B along line A-A.

With reference to FIGS. 4A-4C, one or more interposers 200 may be associated with a printed circuit assembly (PCA) 400 of an implantable medical device having a pinned IMD feedthrough 410. As shown in FIG. 4A, an interposer 200 may be prepackaged and assembled onto a printed circuit board (PCB) portion 402 of the PCA 400 with methods common to the PCA manufacturing industry. For example, with reference to FIG. 4C, solder pads 212 on the solder-pad surface 206 of the interposer 200 and electrical contacts 404 on the side of the PCB portion 402 facing the solder-pad surface of the interposer may be generally axially aligned and fused together during the PCA manufacturing process. The interposers 200, the PCB portion 402 to which the interposers are coupled, and the various other components 406, 408 mounted on other PCB portions form the PCA 400 of the implantable medical device.

With reference to FIGS. 4B and 4C, the PCA 400 of FIG. 4A may be integrated into an implantable medical device having an IMD feedthrough 410 with electrical contacts in the form of pins 412 configured to couple with the interposers 200. The pins 412 extend through a support structure 414 of the IMD feedthrough 410. The weld pads 216 of the interposer 200 are generally axially aligned with the pins 412 of the IMD feedthrough 410 so that the pins fit into and protrude through the holes 222 in the weld pads 216. The portion of the pin 412 which extends above the weld pad of the interposer 200 is fused to the conductive weld pads 216 through a laser welding process. The laser weld process involves the application of laser energy of an appropriate diameter and level to the pin, causing the pin to melt down onto, and fuse with the weld pad 216. The laser weld process results in an electrical connection between the pin 412 and a lead 202 within the interposer 200.

With reference to FIGS. 5A-5D, one or more interposers 200 may be associated with a PCA 500 of an implantable medical device 512 having a leadless IMD feedthrough 510 that presents an electrical contacts in the form of a flat conductive surface 508 instead of a pin 412 (as shown in FIG. 4D). As shown in FIG. 5A, an interposer 200 may be prepackaged and assembled onto a PCB portion 502 of the PCA 500 with methods common to the PCA manufacturing industry. For example, with reference to FIG. 5D, solder pads 212 on the solder-pad surface 206 of the interposer 200 and PCB pads 504 on the side of the PCB portion 502 facing the solder-pad surface of the interposer may be aligned and fused together during the manufacturing process. The interposers 200, the PCB portion 502 to which the interposers are coupled, and various other components 506 mounted on other PCB portions form the PCA 500 of the implantable medical device.

With reference to FIGS. 5B-5D, the PCA 500 of FIG. 5A may be integrated into an implantable medical device 512 having a leadless IMD feedthrough 510 with flat conductive surfaces 508 configured to couple with the interposer 200. To this end, the PCA 500 is integrated into the implantable medical device 512 by aligning the weld-pad vias 218 in the interposer 200 with the flat conductive surfaces 508 of the electrically conductive, leadless vias 514 of the IMD feedthrough 510. The vias 514 extend through a support structure 516 of the IMD feedthrough 510.

After alignment of the interposer 200, the weld pads 216 of the interposer may be laser welded to the flat conductive surfaces 508 of the electrically conductive, leadless vias 514 of the IMD feedthrough 510. Laser welding completes the integration of the interposer 200 into the implantable medical device 512 and provides a plurality of electrically conductive paths between the IMD feedthrough 510 and components of the PCA 500. The electrically conductive paths are formed by the vias 514 of the feedthrough, the leads 202 through the interposer 200, and conductive traces (not shown in any of FIGS. 5A-5D) through the PCB portion 502, which traces are defined in part by PCB pads 504 that connect to the solder pads 212 of the interposer.

Alternate Interposer Configurations

The design and method of manufacture of the interposer component allows for broad flexibility in design to accommodate various implantable medical device configurations.

Figure 6:
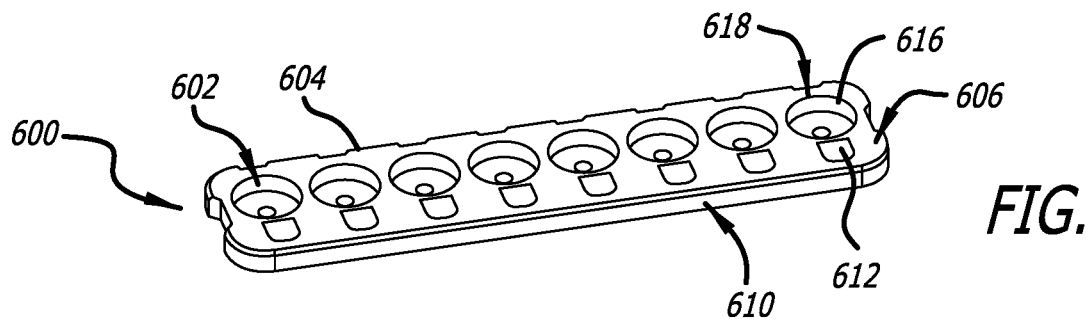
FIG. 6 is an illustration of an interposer of the present disclosure similar to that of FIGS. 2A-2D but with only a single linear array of leads in an over-mold structure.

FIG. 6 is an illustration of an interposer 600 similar to that of FIGS. 2A-2D but with only a single linear array of leads 602 partially embedded in an over-mold structure 604. Note the over-mold structure 604 is illustrated opaque so only the solder pads 612 and weld pads 616 are visible. The leads 602 are considered to lie within or to be bounded by the perimeter 610 of over-mold structure 604 in that no portion of the leads, e.g., the solder pads 612 or the weld pads 616, extend beyond the perimeter. Furthermore, in the configuration of FIG. 6, the solder pads 612 are achieved through exposure of a portion of the lead 602 at the solder-pad surface 606 of the interposer 600. Thus, the solder pads 612 for attachment to the feedthrough are located on the solder-pad surface 606 of the over-mold structure 604 and are thus positioned to be oriented parallel to a surface of a PCA when the interposer 600 is assembled to the PCA.

Figure 7:
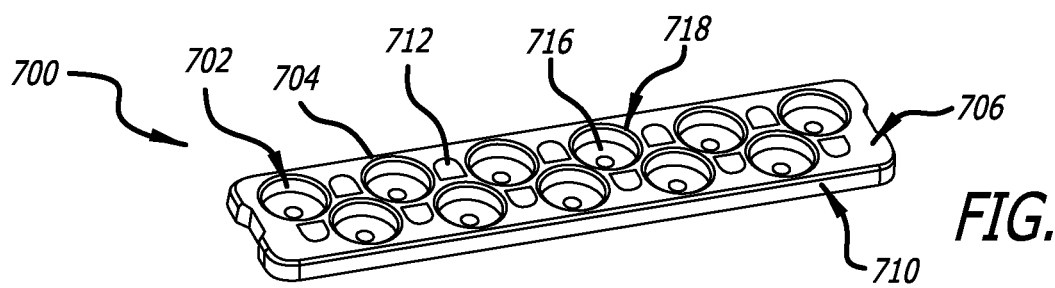
FIG. 7 is an illustration of an interposer of the present disclosure similar to that of FIGS. 2A-2D but with two linear arrays of leads arranged in an over-mold structure such that the solder pads and weld pads of the two arrays combine to form a zig-zag pattern.

FIG. 7 is an illustration of an interposer 700 similar to that of FIGS. 2A-2D but with two linear arrays of leads 702 arranged in an over-mold structure 704 such that the solder pads 712 and weld pads 716 of the two arrays combine to form a zig-zag pattern. The leads 702 are considered to lie within or to be bounded by the perimeter 710 of over-mold structure 704 in that no portion of the leads, e.g., the solder pads 712 or the weld pads 716, extend beyond the perimeter. Furthermore, in the configuration of FIG. 7, the solder pads 712 are achieved through exposure of a portion of the lead 702 at the solder-pad surface 706 of the interposer 700. Thus, the solder pads 712 for attachment to the feedthrough are located on the solder-pad surface 706 of the over-mold structure 704 and are thus positioned to be oriented parallel to the surface of a PCA when the interposer 700 is assembled to the PCA.

Figure 8A:
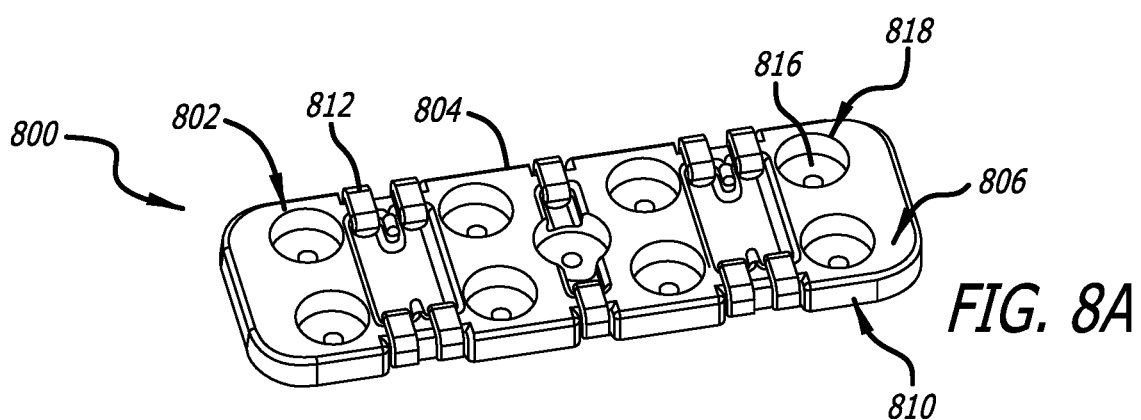
FIGS. 8A-8C are illustrations of an interposer of the present disclosure having leads with a portion that is externally routed over the over-mold structure.
Figure 8B:
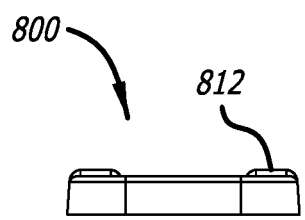
Figure 8C:
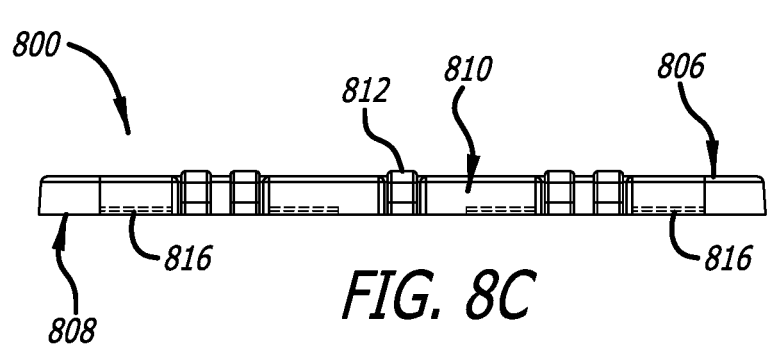

FIGS. 8A-8C are illustrations of an interposer 800 having leads 802 with a portion that is externally routed over the over-mold structure 804. This interposer 800 is manufactured using an different process than that described above for the interposer 200 of FIGS. 2A-2D, 6, and 7. In this different manufacturing process, portions of a lead frame are formed over and around the over-mold structure 804 to achieve the solder pads 812 for attachment to the PCA. The forming of the lead-frame may be performed after the over-mold process. In this alternate manufacturing process the lead-frame is trimmed and then formed around the over-mold to achieve the finished interposer 800. The leads 802 in this configuration are still considered to lie within or to be bounded by the perimeter 810 of over-mold structure 804 in that no portion of the leads, e.g., the solder pads 812 or the weld pads 816, extend beyond the perimeter. Furthermore, in the configuration of FIG. 8, the solder pads 812 are achieved by wrapping a portion of the lead 802 over the perimeter 810 and up to the solder-pad surface 806 of the interposer 800. Thus, the solder pads 812 for attachment to a feedthrough are associated with the solder-pad surface 806 of the over-mold structure 804 and are thus positioned to be oriented parallel to the surface of a PCA when the interposer 800 is assembled to the PCA.

FIGS. 9A and 9B are illustrations of an interposer 900 having leads 902 with portions that are externally routed over the over-mold structure 904 to achieve a pair of opposed solder pads 912a, 912b for each lead 902. The leads 902 are considered to lie partially outside the perimeter 910 of over-mold structure 904 in that the opposed solder pads 912a, 912b extend beyond the perimeter. Furthermore, in the configuration of FIGS. 9A and 9B, the opposed solder pads 912a, 912b are provided by a portion of the lead 902 that extends from the weld pad 916 and bends over the perimeter surface 910 of the interposer 900 to a point generally aligned with the solder-pad surface 906, and then bends outward from the perimeter surface. Thus, the opposed solder pads 912a, 912b for attachment to the feedthrough are located on a plane generally parallel with the solder-pad surface 906 of the over-mold structure 904 and are thus positioned to be oriented parallel to the surface of a PCA when the interposer 900 is assembled to the PCA.

FIGS. 10A-10D are illustrations of an interposer 1000 having a single linear array of leads 1002, each lead with a portion that is externally routed over the over-mold structure 1004 to achieve a solder pads 1012 for attachment to the PCA. The leads 1002 in this configuration are considered to lie within or to be bounded by the perimeter 1010 of over-mold structure 1004 in that no portion of the leads, e.g., the solder pads 1012 or the weld pads 1016, extend beyond the perimeter. Furthermore, in this configuration, the solder pads 1012 for attachment to the feedthrough are located on the perimeter surface 1010 of the over-mold structure 1004 and are thus positioned to be oriented 90 degrees relative to, or orthogonal to the surface of a PCA when the interposer 1000 is assembled to the PCA. This location of the solder pads 1012 is distinct from other interposer configurations disclosed herein, where the solder pads are oriented parallel to the surface of a PCA when the interposer is assembled to the PCA. The 90 degree orientation of the solder pads 1012 enables further design freedom in the orientation of the PCA and the feedthrough pins. For example, the solder pads 1012 may be orthogonal to the electrical contacts of the PCA to which the pads are electrically coupled.

Figure 11A:
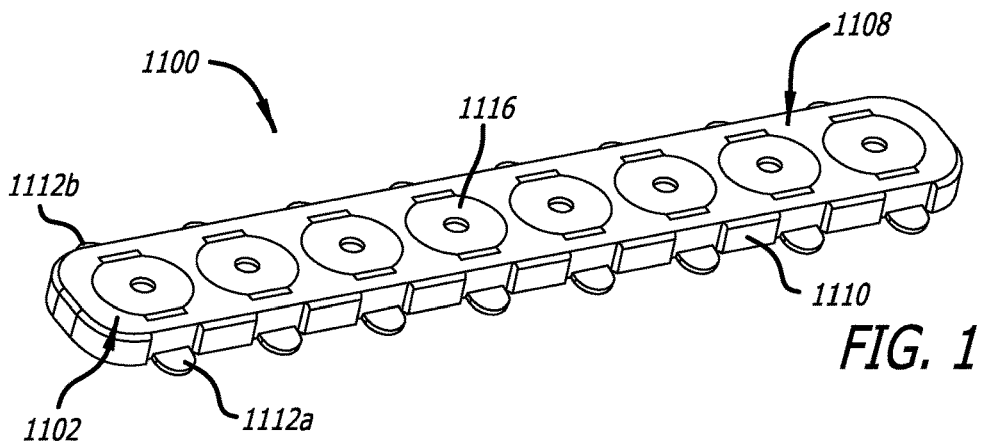
FIGS. 11A and 11B are illustrations of an interposer of the present disclosure having a single linear array of leads, each with portions that extend from the over-mold structure to achieve a pair of opposed solder pads for each lead.
Figure 11B:
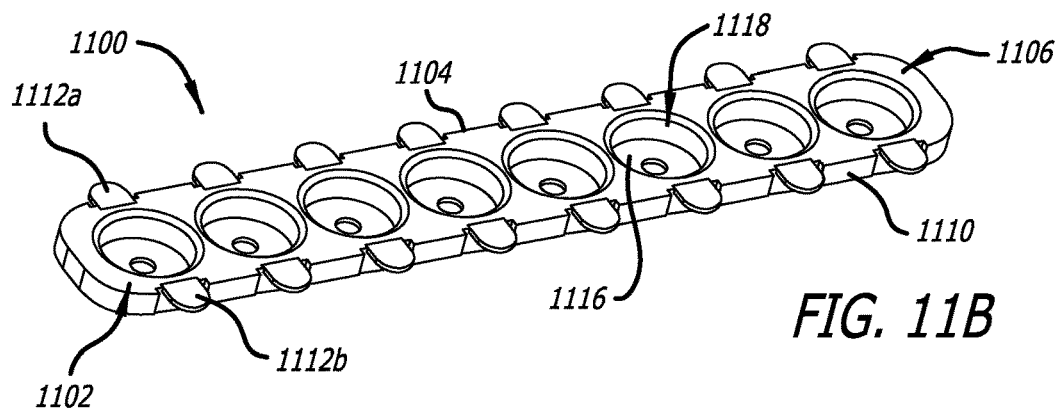

FIGS. 11A and 11B are illustrations of an interposer 1100 having a single linear array of leads 1102 with portions that extend from the over-mold structure 1104 to achieve a pair of opposed solder pads 1112a, 1112b for each lead 1102. The leads 1102 are considered to lie partially outside the perimeter 1110 of over-mold structure 1104 in that the opposed solder pads 1112a, 1112b extend beyond the perimeter. Furthermore, in the configuration of FIGS. 11A and 11B, the opposed solder pads 1112a, 1112b are provided by a portion of the lead 1102 that is embedded in the over-mold structure 1104 and that extends from the weld pad 1116 and bends over the perimeter surface 1110 of the interposer 1100 to a point generally aligned with the solder-pad surface 1106, and then bends outward to exit the over-mold structure 1104 and extend beyond the perimeter surface. Thus, the opposed solder pads 1112a, 1112b for attachment to the feedthrough are located on a plane generally parallel with the solder-pad surface 1106 of the over-mold structure 1104 and are thus positioned to be oriented parallel to the surface of a PCA when the interposer 1100 is assembled to the PCA. It is noted that this interposer 1100 is similar to that of FIGS. 9A and 9B except that a portions of the leads 1102 are embedded in the over-mold structure 1104 instead of being fully exposed.

Figure 12A:
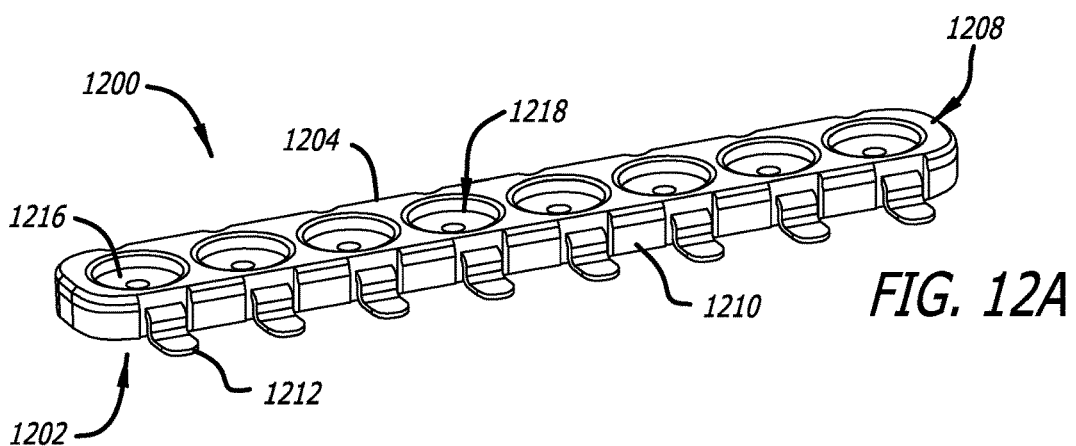
FIGS. 12A and 12B are illustrations of an interposer of the present disclosure having a single linear array of leads, each with a portion that extends from the mid-span of the over-mold structure to achieve a single solder pad for each lead.
Figure 12B:
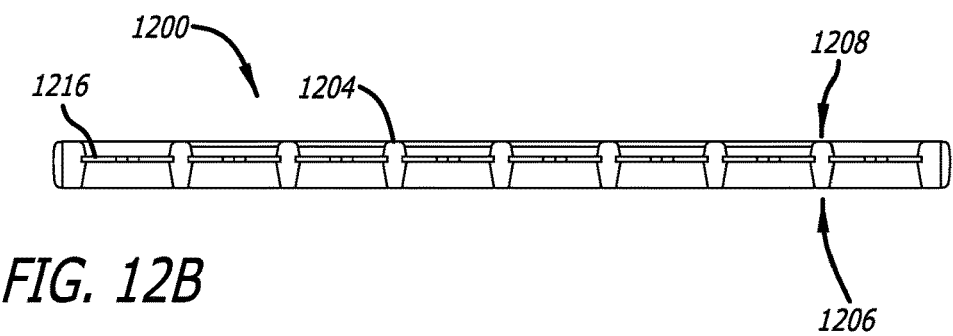

FIGS. 12A and 12B are illustrations of an interposer 1200 having a single linear array of leads 1202, each with a weld pad 1216 located in the mid-span of the over-mold structure 1204. In the manufacture process of this interposer 1200, the lead-frame is molded in the mid-span of the over-mold structure 1204 where the over-mold material covers both sides of the weld pad 1216 of the lead frame. This alternate configuration helps reduces the risk of dislodging the over-mold structure 1204 from the lead frame 302. This configuration is applicable to attachment to feedthrough pins and is not amenable to attached to leadless feedthrough pads since the weld pads 1216 are not flush with the weld-pad surface 1208. In this configuration, locking tabs (e.g., 214 in FIG. 2B) are not required when the lead-frame is molded into the mid-span of the over-mold structure 1204.

The leads 1202 are considered to lie partially outside the perimeter 1210 of over-mold structure 1204 in that the solder pads 1212 extend beyond the perimeter. Furthermore, in the configuration of FIGS. 12A and 12B, the solder pads 1212 are provided by a portion of the lead 1202 that is embedded in the over-mold structure 1204 and that extends from the weld pad 1216 to exit the over-mold structure and bend over the perimeter surface 1210 of the interposer 1200 to a point generally aligned with the solder-pad surface 1206, and then bends outward beyond the perimeter surface. Thus, the solder pad 1212 for attachment to the feedthrough are located on a plane generally parallel with the solder-pad surface 1206 of the over-mold structure 1204 and are thus positioned to be oriented parallel to the surface of a PCA when the interposer 1200 is assembled to the PCA.

Combinations of the various alternative embodiments described may be interchangeable. For example, molding the laser weld pad within the mid-span of the over-mold frame may be applied to a component either with the lead frame formed within our or outside the over-mold frame. Similarly, the solder pads may be located within the over-mold or outside the over-mold frame while the solder pad is oriented parallel or orthogonal to the laser weld pad.

Thus, with reference to FIGS. 4A-4C, disclosed herein are various embodiments of PCAs 400 for coupling to an IMD feedthrough 410 of an implantable medical device. The IMD feedthrough 410 has a support structure 414 and a plurality of IMD electrical contacts 412 extending through the support structure. In general, the PCA 400 includes a PCB portion 402 and an interposer 200. The PCB portion 402 is configured to be arranged relative to the support structure 414 of the IMD feedthrough 410 and includes a plurality of electrical contacts 404. The interposer 200 is secured to the PCB portion 402 and includes a dielectric over-mold structure 204 and a plurality of leads 202. The number of leads 202 may correspond in number to the plurality of PCB electrical contacts 404 of the PCB portion 402. Each lead 202 is integrated with the dielectric over-mold structure 204 and includes a weld pad 216 and a solder pad 212. Each solder pads 212 of the interposer 200 is electrically coupled to a corresponding PCB electrical contacts 404 of the PCB portion to provide an alignment between one or more weld pads 216 of the interposer 200 and one or more corresponding IMD electrical contacts 412 of the IMD feedthrough 410.

With reference to FIGS. 3F-12B, the dielectric over-mold structure 204, 604, 704, 804, 904, 1004, 1104, 1204 has a solder-pad surface 206, 606, 706, 806, 906, 1006, 1106, 1206 and a weld-pad surface 208, 808, 908, 1008, 1108, 1208 opposite the solder-pad surface, and a perimeter surface 210, 610, 710, 810, 910, 1010, 1110, 1210 around the perimeter of the dielectric over-mold structure that is generally orthogonal to the weld-pad surface and the solder-pad surface.

In some embodiments of the interposer, such as shown in FIGS. 3F and 3G, the solder pads 212 of the interposer 200 are generally coplanar with the solder-pad surface 206 of the dielectric over-mold structure 204, and the weld pads 216 are generally co-planar with the weld-pad surface 208. The dielectric over-mold structure 204 includes a plurality of solder-pad vias 220, each having an end that exposes a surface of a corresponding solder pad 212, and a plurality of weld-pad vias 218, each having an end that exposes a surface of a corresponding weld pad 216.

With reference to FIGS. 8A-8C and 10A-10D, in some embodiments of the interposer, the solder pads 812, 1012 are associated with the perimeter surface 810, 1010 of the dielectric over-mold structure 804, 1004. The weld pads 816 are generally coplanar with the weld-pad surface 808 of the dielectric over-mold structure 804, 1004. The dielectric over-mold structure 804, 1004 includes a plurality of weld-pad vias 818, 1018, each having an end that exposes a surface of a corresponding weld pad 816, 1016.

With reference to FIGS. 9A-9B and 11A-11B, in some embodiments of the interposer 900, 1100, the solder pads 912a, 912b, 1112a, 1112b are outside the perimeter 910, 1110 of the dielectric over-mold structure 904, 1104, and lie in a plane aligned with the solder-pad surface 906, 1106 of the dielectric over-mold structure. The weld pads 916, 1116 are generally coplanar with the weld-pad surface 908, 1108 of the dielectric over-mold structure 904, 1104. The dielectric over-mold structure 904, 1104 includes a plurality of weld-pad vias 918, 1118, each having an end that exposes a surface of a corresponding weld pad 916, 1116.

With reference to FIGS. 12A-12B, in some embodiment of the interposer 1200, the weld pads 1216 lie in a plane between the weld-pad surface 1208 of the dielectric over-mold structure 1204 and the solder-pad surface 1206 of the dielectric over-mold structure. The dielectric over-mold structure 1204 comprises a plurality of weld-pad vias 1218, each having an end that exposes a surface of a corresponding weld pad 1216. The solder pads 1212 are outside the perimeter 1210 of the dielectric over-mold structure, and lie in a plane aligned with the solder-pad surface 1206 of the dielectric over-mold structure 1204.

The apparatuses, e.g., interposers, disclosed provide means of establishing electrical interconnection between a feedthrough and a printed circuit assembly of an active implantable medical device. The apparatuses and methods have the following advantages:

The interposers include multiple electrical connects, including ground signals, which reduces the complexity of implantable medical device interconnect design. The interposers also reduce the physical size of interconnects to facilitate miniaturization of medical devices.

A method of manufacture of the interposers provides flexibility of design to achieve a variety of configurations, including the size, shape, routing, location and the number of discrete traces depending on need.

The interposers can be fabricated with metal forming and injection molding methods of manufacture suitable for high volume production and relatively low cost. The interposers are suitable for automated assembly methods common in the printed circuit assembly industry, such as tape-and-real component packaging and robotic pick and place delivery, to achieve multiple discrete electrical connections to a printed circuit assembly.

The interposers are suitable for, and facilitate laser welding processes between a feedthrough pin and a laser weld pad in the interposer. This eliminates the need for discreet wires between the feedthrough and the PCA of the device. The interposers facilitate laser welding to a conductive pad in a high temperature co-fire ceramic (leadless) implantable feedthrough. The interposers do not require continual physical clamping of the interposer to maintain the electrical connection as with other interposer interconnects, such as is required with spring loaded interposer electrical connections.

Single Pin Interposer

Figure 13:
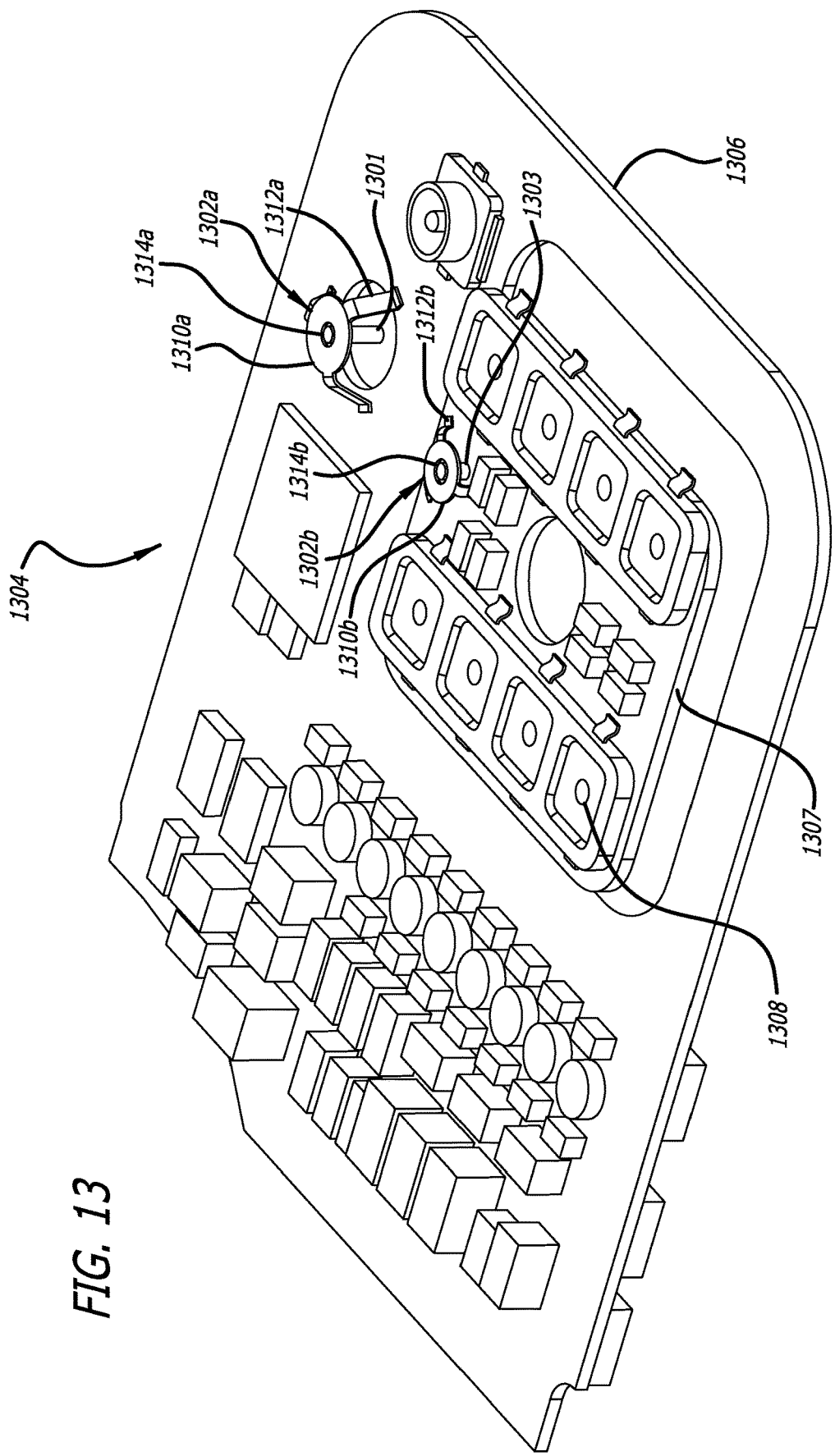
FIG. 13 is an illustration of a PCA including a pair of single pin interposers electrically coupled to different PCB portions of the PCA.

With reference to FIG. 13, in another embodiment, an interposer 1302a, 1302b of an active implantable medical device is configured and arranged to provide an electrical interface between a component of the medical device and a printed circuit assembly (PCA) 1304 of the medical device. To this end, a single pin connector 1301, 1303 electrically coupled to the component of the medical device extends through a printed circuit board (PCB) 1306 of the PCA 1304 and couples with the interposer 1302a, 1302b. A single pin interposer 1302a, 1302b is useful for a single electrical connection not associated with an array of feedthrough pins 1308.

In the example shown in FIG. 13, one interposer 1302a may connect to a long range telemetry pin 1301 that extends through a hole of the PCB 1306 and couples with an antenna (not shown) of the medical device. The other interposer 1302b may connect with a pin 1303 that extends through a feedthrough portion 1307 of the PCB 1306 and couples to the housing of the medical device that functions as a return electrode.

The single pin interposer 1302a, 1302b includes an electrically conductive frame having a single weld pad 1310a, 1310b and a plurality of legs 1312a, 1312b. While the weld pads 1310a, 1310b shown in FIG. 13 are disc shaped, other shapes a contemplated. The weld pad 1310a, 1310b includes a hole 1314a, 1314b sized to receive a pin connector 1301, 1303. The legs 1312a, 1312b are configured to be secured to the surface of the PCB 1306, with at least one of the legs being electrically coupled, e.g. soldered or surface mounted, to the PCB to thereby provide an electrical coupling between the PCB and the component, e.g., antenna, return electrode, coupled to the pin connector 1301, 1303. The legs 1312a, 1312b are also configured to position or offset the weld pad 1310a, 1310b away from the surface of the PCB. While the weld pads 1310a, 1310b shown in FIG. 13 are in a generally parallel-plane relationship with a planar surface of the PCB 1306, other non-parallel arrangements are possible. The interposer 1302a, 1302b may further include a plastic molded body that covers portions of electrically conductive frame and provides support to the frame.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A printed circuit assembly (PCA) for coupling to an IMD feedthrough of an implantable medical device, the IMD feedthrough having a support structure and a plurality of electrical contacts extending through the support structure, the PCA comprising:

a printed circuit board (PCB) portion configured to be arranged relative to a surface of the support structure of the IMD feedthrough, the PCB portion comprising a plurality of electrical contacts on a side of the PCB portion facing away from the surface of the support structure; and at least one interposer secured to the side of the PCB portion facing away from the surface of the support structure, the interposer comprising:
 a dielectric over-mold structure, and
 a plurality of leads, each lead integrated with the dielectric over-mold structure and comprising a weld pad and a solder pad,
wherein one or more solder pads of the interposer are electrically coupled by surface-to-surface contact with one or more corresponding electrical contacts of the PCB portion to provide an alignment between one or more weld pads of the interposer and one or more corresponding electrical contacts of the IMD feedthrough.

2. The printed circuit assembly of claim 1, wherein the dielectric over-mold structure is characterized by a weld-pad surface, a solder-pad surface opposite the weld-pad surface, and a perimeter surface around the perimeter of the dielectric over-mold structure and generally orthogonal to the weld-pad surface and the solder-pad surface.

3. The printed circuit assembly of claim 2, wherein:
the weld pads are generally co-planar with the weld-pad surface of the dielectric over-mold structure; and
the dielectric over-mold structure comprises a plurality of weld-pad vias, each having an end that exposes a surface of a corresponding weld pad.

4. The printed circuit assembly of claim 2, wherein:
the solder pads are generally coplanar with the solder-pad surface of the dielectric over-mold structure, and
the dielectric over-mold structure comprises a plurality of solder-pad vias, each having an end that exposes a surface of a corresponding solder pad.

5. The printed circuit assembly of claim 1, wherein the plurality of leads are partially embedded in the dielectric over-mold structure.

6. The printed circuit assembly of claim 1, wherein one or more solder pads of the interposer are fused with one or more corresponding electrical contacts of the PCB portion.

7. A printed circuit assembly (PCA) for coupling to an IMD feedthrough of an implantable medical device, the IMD feedthrough having a support structure and a plurality of electrical contacts extending through the support structure, the PCA comprising:
a printed circuit board (PCB) portion configured to be arranged relative to the support structure of the IMD feedthrough, the PCB portion comprising a plurality of electrical contacts; and
at least one interposer secured to the PCB portion, the interposer comprising:
 a dielectric over-mold structure, and
 a plurality of leads, each lead integrated with the dielectric over-mold structure and comprising a weld pad and a solder pad,
wherein:
one or more solder pads of the interposer are electrically coupled to one or more corresponding electrical contacts of the PCB portion to provide an alignment between one or more weld pads of the interposer and one or more corresponding electrical contacts of the IMD feedthrough;

the dielectric over-mold structure is characterized by a weld-pad surface, a solder-pad surface opposite the weld-pad surface, and a perimeter surface around the perimeter of the dielectric over-mold structure and generally orthogonal to the weld-pad surface and the solder-pad surface;
the weld pads are generally coplanar with the weld-pad surface of the dielectric over-mold structure;
the dielectric over-mold structure comprises a plurality of weld-pad vias, each having an end that exposes a surface of a corresponding weld pad; and
the solder pads are associated with the perimeter surface of the dielectric over-mold structure.

8. The printed circuit assembly of claim 7, wherein the plurality of leads are partially embedded in the dielectric over-mold structure.

9. A printed circuit assembly (PCA) for coupling to an IMD feedthrough of an implantable medical device, the IMD feedthrough having a support structure and a plurality of electrical contacts extending through the support structure, the PCA comprising:
a printed circuit board (PCB) portion configured to be arranged relative to the support structure of the IMD feedthrough, the PCB portion comprising a plurality of electrical contacts; and
at least one interposer secured to the PCB portion, the interposer comprising:
 a dielectric over-mold structure, and
 a plurality of leads, each lead integrated with the dielectric over-mold structure and comprising a weld pad and a solder pad,
wherein:
one or more solder pads of the interposer are electrically coupled to one or more corresponding electrical contacts of the PCB portion to provide an alignment between one or more weld pads of the interposer and one or more corresponding electrical contacts of the IMD feedthrough;
the dielectric over-mold structure is characterized by a weld-pad surface, a solder-pad surface opposite the weld-pad surface, and a perimeter surface around the perimeter of the dielectric over-mold structure and generally orthogonal to the weld-pad surface and the solder-pad surface;
the weld pads are generally coplanar with the weld-pad surface of the dielectric over-mold structure;
the dielectric over-mold structure comprises a plurality of weld-pad vias, each having an end that exposes a surface of a corresponding weld pad; and
the solder pads are outside the perimeter of the dielectric over-mold structure.

10. The printed circuit assembly of claim 9, wherein the solder pads lie in a plane aligned with the solder-pad surface of the dielectric over-mold structure.

11. The printed circuit assembly of claim 9, wherein the plurality of leads are partially embedded in the dielectric over-mold structure.

12. A printed circuit assembly (PCA) for coupling to an IMD feedthrough of an implantable medical device, the IMD feedthrough having a support structure and a plurality of electrical contacts extending through the support structure, the PCA comprising:
a printed circuit board (PCB) portion configured to be arranged relative to the support structure of the IMD feedthrough, the PCB portion comprising a plurality of electrical contacts; and at least one interposer secured to the PCB portion, the interposer comprising:

a dielectric over-mold structure, and a plurality of leads, each lead integrated with the dielectric over-mold structure and comprising a weld pad and a solder pad, wherein:

one or more solder pads of the interposer are electrically coupled to one or more corresponding electrical contacts of the PCB portion to provide an alignment between one or more weld pads of the interposer and one or more corresponding electrical contacts of the IMD feedthrough;

the dielectric over-mold structure is characterized by a weld-pad surface, a solder-pad surface opposite the weld-pad surface, and a perimeter surface around the perimeter of the dielectric over-mold structure and generally orthogonal to the weld-pad surface and the solder-pad surface;

the weld pads lie in a plane between the weld-pad surface of the dielectric over-mold structure and the solder-pad surface of the dielectric over-mold structure;

the dielectric over-mold structure comprises a plurality of weld-pad vias, each having an end that exposes a surface of a corresponding weld pad; and the solder pads are outside the perimeter of the dielectric over-mold structure.

13. The printed circuit assembly of claim 12, wherein the solder pads lie in a plane aligned with the solder-pad surface of the dielectric over-mold structure.

14. The printed circuit assembly of claim 12, wherein the plurality of leads are partially embedded in the dielectric over-mold structure.

* * * * *